US012662654B2

(12) United States Patent　　(10) Patent No.:　US 12,662,654 B2
Rothbauer et al.　　　　　　　　(45) Date of Patent:　　Jun. 23, 2026

(54) MICROFLUIDIC DEVICE

(71) Applicant: Technische Universität Wien, Vienna (AT)

(72) Inventors: Mario Rothbauer, Pfaffstätten (AT); Peter Ertl, Vienna (AT); Silvia Schobesberger, Vienna (AT)

(73) Assignee: Technische Universität Wien, Vienna (AT)

( * ) Notice: Subject to any disclaimer, the term of this patent is extended or adjusted under 35 U.S.C. 154(b) by 816 days.

(21) Appl. No.: 17/923,534

(22) PCT Filed: May 5, 2021

(86) PCT No.: PCT/EP2021/061859
§ 371 (c)(1),
(2) Date: Nov. 4, 2022

(87) PCT Pub. No.: WO2021/224328
PCT Pub. Date: Nov. 11, 2021

(65) Prior Publication Data
US 2023/0203417 A1　　Jun. 29, 2023

(30) Foreign Application Priority Data

May 8, 2020　(EP) ..................................... 20173705

(51) Int. Cl.
*C12M 3/06*　　　(2006.01)
*C12M 1/00*　　　(2006.01)
(Continued)

(52) U.S. Cl.
CPC ............ *C12M 23/16* (2013.01); *C12M 21/08* (2013.01); *C12M 23/20* (2013.01); *C12M 23/34* (2013.01); *G01N 33/5082* (2013.01)

(58) Field of Classification Search
CPC ..... B01L 2300/0816; B01L 2300/0829; B01L 3/502715; C12M 21/08; C12M 23/16;
(Continued)

(56) References Cited

U.S. PATENT DOCUMENTS

2011/0236970 A1*　9/2011　Larsen ................... C12M 23/12
　　　　　　　　　　　　　　　　　　　435/395
2013/0059322 A1　　3/2013　Hung et al.
(Continued)

FOREIGN PATENT DOCUMENTS

WO　　　2009/039433 A1　　3/2009

OTHER PUBLICATIONS

European Search Report received for EP Patent Application No. 20173705.3, mailed on Oct. 28, 2020, 6 pages.
(Continued)

*Primary Examiner* — Jennifer Wecker
*Assistant Examiner* — Jonathan Bortoli
(74) *Attorney, Agent, or Firm* — Workman Nydegger

(57) ABSTRACT

The present invention relates to a microfluidic device (1), preferably for producing a three-dimensional cell culture, having at least one chamber (2), and a fluid channel (3) which flows through at least part of the chamber (2) in order to provide a fluid stream which flows through the chamber (2) preferably continuously, wherein the chamber (2) is connected to a loading opening (4) and via the loading opening (4) can be loaded with hydrogel up to a desired fill level, characterized in that the chamber (2) comprises a main chamber (5) and a secondary chamber (6) connected to the main chamber (5), wherein, when the chamber (2) is being loaded with hydrogel up to the desired fill level, the secondary chamber is at least partially filled with hydrogel backed up from the main chamber (5).

17 Claims, 8 Drawing Sheets

(51) Int. Cl.
    *C12M 3/00*        (2006.01)
    *G01N 33/50*     (2006.01)
(58) Field of Classification Search
    CPC ... C12M 23/20; C12M 23/34; G01N 33/4833;
                                       G01N 33/5082
    See application file for complete search history.

(56) References Cited

U.S. PATENT DOCUMENTS

| | | | |
|---|---|---|---|
| 2019/0009274 A1* | 1/2019 | Novak | G01N 33/5088 |
| 2019/0390149 A1* | 12/2019 | Cho | C12M 23/12 |
| 2020/0063081 A1 | 2/2020 | Vulto et al. | |
| 2020/0238278 A1* | 7/2020 | Fraden | B01L 3/0265 |
| 2021/0087515 A1* | 3/2021 | Allbritton | C12M 25/04 |

OTHER PUBLICATIONS

International Preliminary Report on Patentability received for PCT Patent Application No. PCT/EP21/061859, mailed on Nov. 17, 2022, 14 pages (7 pages of English Translation and 7 pages of Original Document).

International Search Report and Written Opinion received for PCT Patent Application No. PCT/EP21/061859, mailed on Sep. 2, 2021, 16 pages (8 pages of English Translation and 8 pages of Original Document).

Rothbauer et al., "Tomorrow today: organ-on-a-chip advances towards clinically relevant pharmaceutical and medical in vitro models", Current Opinion in Biotechnology, 2019, vol. 55, pp. 81-86.

Rothbauer et al., "Recent advances in microfluidic technologies for cell-to-cell interaction studies", Lab Chip., 2018, vol. 18, pp. 249-270.

Rothbauer et al., "Recent advances and future applications of microfluidic live-cell microarrays", Biotechnology Advances, vol. 33, Jun. 30, 2015, pp. 948-961.

Kratz et al., "Latest Trends in Biosensing for Microphysiological Organs-on-a-Chip and Body-on-a-Chip Systems", Sep. 19, 2019, Biosensors, vol. 9, No. 110, pp. 1-25.

Huh et al., "Reconstituting Organ-Level Lung Functions on a Chip", Science, Jun. 25, 2010, vol. 328, No. 5986, pp. 1662-1668.

* cited by examiner

MICROFLUIDIC DEVICE

TECHNICAL FIELD

The present invention relates to the field of microfluidic devices.

BACKGROUND OF THE INVENTION 3D models of animal and, in particular, human cells make it possible to reconstruct animal or human tissue in vitro. However, until now, important physiological conditions such as the application of mechanical forces or diffusion gradients could only be simulated to a limited extent, although they are of great importance for the functionality of 3D cell constructs. To solve this problem, 3D cell culture techniques have been combined with microfluidics, making this 3D cultivation method, referred to as organ-on-a-chip, more physiologically relevant.

The term "organ-on-a-chip" was created in 2010 by Donald Ingber, who published a lung model on a microchip with organ-level functions (Huh, D., et al, Science, 2010. 328(5986): p. 1662-8).

The main advantage of organ-on-a-chip is the precise spatially resolved control over molecule and fluids, making it possible to reflect physiological molecular gradients and flows. In addition, this control allows different cell types to be cultured together in a controlled manner, leading to more body-like organoid functions or vascularization of the microchips.

The defined chambers and channels of microfluidic devices provide a reproducible 3D cell culture surface and result in reduced consumption of cells and nutrient medium due to the reduced dimensions on the microchip. In addition, because animal- or human-derived cells are used, organ-on-a-chip is expected to lead to the generation of more pharmaceutically relevant data than animal experiments.

In particular in drug development, the translation of animal studies to human physiology during clinical trials often leads to rejection of the drug—a financial burden for companies. Organs-on-a-chip as disease models can be used to identify new targets for disease control, on the one hand, and to evaluate the toxicity and efficacy of existing active ingredients, on the other. Organs-on-a-chip represent an intermediate level of complexity between conventional 3D cell cultures and mouse models, allowing for more accurate active ingredient development as complexity increases, which could increase the number of active ingredients approved after clinical trials.

To date, many different organs, such as lung, intestine, kidney, or placenta, as well as vascular and lymphatic models and heart and liver models, have been grown on chips.

Moreover, the technology of induced pluripotent stem cells opened the possibility of developing brain models based on organoids. Since stem cells can be differentiated into any cell type, it is possible to develop personalized microchips using individual stem cells.

The application of organ-on-a-chip remains a challenge as the 3D culture on the chip should represent all the major functions of an organ. Such model systems must have high reproducibility to be considered a valid alternative to animal models. In order to make hydrogel-based organ-on-a-chip systems more reproducible, not only the cellular aspects (cell-cell variance and heterogeneity) but also the technological framework for the tool must be made as user-friendly as possible. This user-friendliness is often questionable, especially for organ-on-a-chip developed in the academic research environment, as these microchips are usually developed and operated by trained scientific personnel. For industrialization and commercial marketing, it is therefore necessary to optimize the design of organs-on-a-chip developed in a scientific context with regard to handling in order to be able to guarantee reproducible use by untrained personnel.

US 2013/059322 A1 discloses a microfluidic device for producing a three-dimensional cell culture comprising a chamber.

US 2020/063081 A1 discloses a microfluidic device for producing a cell culture.

WO 2009/039433 A1 discloses a microfluidic system comprising a sensor in a microfluidic device to determine conditions prevailing in the device.

Conventional organ-on-a-chip devices typically include chambers in which an organoid can be formed by adding appropriate cells. Since due to cell aggregations, the organoid formed in the chambers has a smaller volume than the chambers in which the organoid is located, the formed organoids in the chambers move according to current conditions. That is, a measurement (e.g., an optical measurement) directly on the organoids is either not feasible or difficult to perform, which does not lead to a reproducible result. It is therefore an object of the present invention to provide means and methods that enable organoids to be positioned within chambers of microfluidic devices at a defined location within the chambers in order to ensure the lowest possible mobility of the organoids.

Another object of the present invention is to provide chambers of microfluidic devices adjacent to and in contact with a fluid channel that allow hydrogel, which is advantageous as a matrix for the formation of organoids, to be introduced into the chambers without penetrating into the fluid channel.

SUMMARY OF THE INVENTION

According to the invention, these objects are achieved by a microfluidic device with at least one chamber and a fluid channel at least partially extending through the chamber for providing a fluid stream preferably continuously passing through the chamber, wherein the chamber is connected to a loading opening and can be loaded with hydrogel via the loading opening up to a desired fill level, wherein the chamber comprises a main chamber and a secondary chamber connected to the main chamber, wherein, when the chamber is being loaded with hydrogel up to the desired fill level, the secondary chamber is at least partially filled with hydrogel backed up from the main chamber. This means that the secondary chamber is designed to be at least partially filled with hydrogel backed up from the main chamber when the chamber is being loaded with hydrogel up to the desired fill level.

The microfluidic device according to the invention preferably for producing a three-dimensional cell culture, in particular an organoid, comprises at least one chamber and a fluid channel extending at least partially through the chamber for providing a fluid stream preferably continuously passing through the chamber. The chamber is connected to a loading opening and can be loaded with hydrogel via the loading opening up to a desired fill level. The chamber further comprises a main chamber and a secondary chamber connected to the main chamber, wherein, when the chamber is being loaded with hydrogel to the desired fill level, the secondary chamber can at least partially be filled with hydrogel.

The division of the chamber into a main chamber and a secondary chamber, in conjunction with the fact that when the main chamber is filled with hydrogel to the desired fill level, the secondary chamber is also at least partially filled with hydrogel, has the advantage that when the three-dimensional cell culture is formed, a portion of the cell culture, and primarily a portion of the hydrogel that condenses over time, forms in the secondary chamber. By means of this portion located in the secondary chamber, the entire cell culture is fixed in the chamber, thus preventing the cell culture from slipping in the chamber. This improves the reproducibility of tests and experiments performed on the cell culture with different cell cultures produced in multiple devices according to the invention.

Another aspect of the present invention relates to a carrier comprising at least one microfluidic device according to the present invention.

The microfluidic device according to the present invention can be placed onto a solid carrier. In order to be able to simultaneously perform as many examinations as possible, it is particularly preferred that the carrier comprises two or more of the devices according to the invention.

Yet another aspect of the present invention relates to a method for producing a three-dimensional cell culture or an organoid using a microfluidic device according to the invention, comprising a step (A) of loading a chamber of the device through a loading opening with hydrogel to a desired fill level.

With the device according to the invention, three-dimensional cell cultures or organoids can be produced by introducing corresponding cells into the device. To ensure the stability of the cell cultures or organoids, hydrogel is used as the matrix.

Another aspect of the present relates to methods for determining the influence of a chemical compound and/or at least one physical parameter on cells of a three-dimensional cell culture in a microfluidic device according to the invention, comprising the steps:

a) detecting a first state of the cells, b1) contacting the cells with a chemical compound and/or b2) changing a physical parameter within the microfluidic device, c) detecting a second state of the cells, and d) determining the influence of the chemical compound and/or the at least one physical parameter on the cells by identifying a difference between the first state and second state of the cells.

The device of the present invention can be used to investigate the influence of a chemical compound and/or at least one physical parameter on cells, in particular on a cell culture or organoid located in the chamber of the device according to the invention. In particular, by fixing the cell culture or organoid within the chamber, it is now possible to generate reproducible data since a possible measurement point on the cell culture or organoid in the chambers is constant. In addition, media and solutions can be reproducibly delivered to the cells in the chambers via the fluid channel.

DESCRIPTION OF EMBODIMENTS

Figure 1:
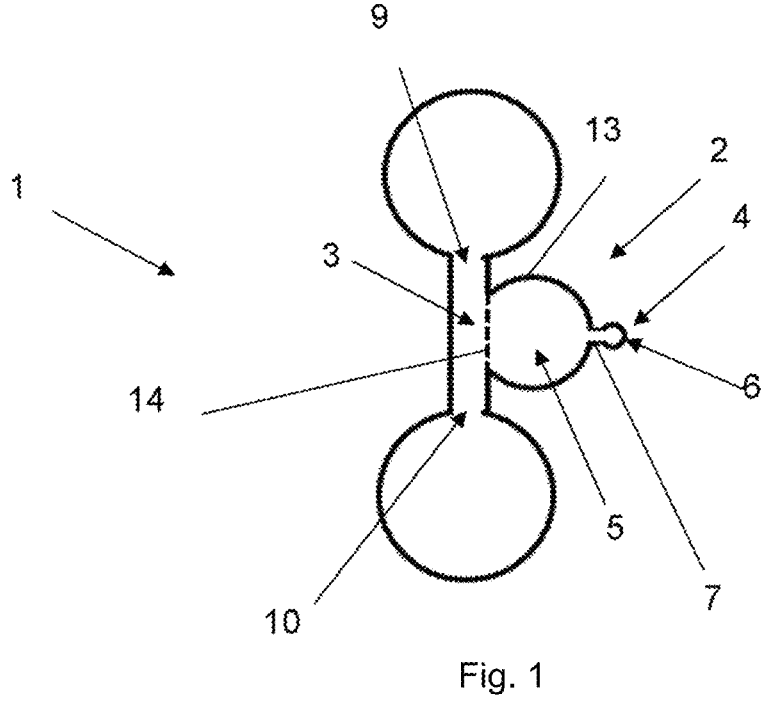
FIG. 1 shows a microfluidic device according to the invention in a top view.

The device according to the invention, which can be produced according to known prior art methods (see, for example, Rothbauer M et al. (Lab Chip, 2018, 18, 249-270); Rothbauer M et al. (Biotech Adv, 2015, 33, 948-961); Rothbauer M et al. (Curr Opin Biotech, 2019, 55, 81-86)), is particularly suitable for the production of three-dimensional cell cultures and organoids and for the simulation of in vivo-like conditions. Especially the ability to flow a fluid around the cell cultures or the organoids is particularly advantageous with the device according to the invention.

Three-dimensional cell cultures have the advantage that the cells therein adopt a spatial orientation, similar to organs in the body of a human or animal. Such cell cultures consist of multiple cell layers, resulting in their three-dimensionality. To facilitate shaping, it is advantageous to add, for example, scaffold proteins/hydrogels such as collagen or Matrigel® to the cells. It has been shown that many cell lines form spheroids in a three dimensional environment.

In many areas of research, there is an increased use of three-dimensional cell cultures to perform certain studies in an environment similar to or mimicking nature. As an example, reference is made to pharmaceutical research, which—in order to reduce the number of costly animal experiments in the initial phase of research projects-uses three-dimensional cell cultures. Since three-dimensional cell cultures can exhibit organ-like behavior, meaningful results about the mode of action of an active ingredient can be obtained, which even allow conclusions to be drawn with regard to pharmacokinetics and pharmacodynamics.

Organoids are generally organ-like microstructures only a few millimeters in size that can be produced using the device according to the invention. Typically, organoids are grown from tissue cells, embryonic stem cells, or induced pluripotent stem cells. Despite the fact that they have no stroma and no vessels, they nevertheless exhibit physiologically relevant organ-like properties. Currently, organoids are known for heart, stomach, intestine, kidney and brain.

According to the invention, the chamber of the device according to the invention can be loaded to a "desired fill level". "Desired fill level", as used herein, means that as much hydrogel can be loaded into the chamber until its main chamber and its secondary chamber are filled with hydrogel. In any case, the secondary chamber must also comprise hydrogel to form the anchor point of the forming three-dimensional cell culture or organoid.

Preferably, the main chamber and the secondary chamber are connected by a connecting channel, wherein the connecting channel has a smaller cross section than the main chamber and the secondary chamber. As a result of this, the advantage is achieved that the cell culture is fixed even stronger by the cross-sectional constriction between the main chamber and the secondary chamber, and the position of the cell culture is precisely defined.

By providing such a cross-sectional constriction between the main chamber and the secondary chamber, it is ensured in an even more efficient and better manner that when the cell aggregates or organoids are formed in the main chamber, they retract towards the loading opening in a controlled manner. It is ensured that this process takes place in a controlled manner and always in the same way. Changes of the three-dimensional cell aggregates or organoids can be tracked microscopically and due to the defined position of the three-dimensional cell aggregates/cultures or organoids, microscopes can be fixed and automated, for example.

According to a preferred embodiment of the device of the invention, the fluid channel at least partially extends through the main chamber, and the main chamber comprises a first chamber bottom. The fluid channel further comprises a fluid inlet arranged spaced apart from the first chamber bottom in the main chamber, and a fluid outlet arranged spaced apart from the first chamber bottom in the main chamber. As a result of this, the advantage is achieved that a step is formed between the main chamber and the fluid inlet and the fluid outlet, respectively, which prevents hydrogel from flowing into the fluid inlet and the fluid outlet, respectively, during loading of the chamber.

Preferably, the main chamber has a first chamber bottom and the secondary chamber has a second chamber bottom, wherein the first chamber bottom is formed at a lower height level than the second chamber bottom. As a result of this, the advantage is achieved that the majority of the hydrogel accumulates in the main chamber, and the secondary chamber provides an anchorage for a cell culture largely produced or grown in the main chamber.

Expediently, the fluid channel has a fluid channel bottom, wherein the fluid channel bottom is formed at a higher height level than the first chamber bottom. This prevents hydrogel from flowing through the fluid channel when loading the chamber.

According to the preferred embodiment of the device according to the invention, the fluid channel bottom is formed at a lower height level than the second chamber bottom. As a result of this, a reservoir for hydrogel in which the cell culture can grow is formed in the main chamber. The difference in height between the fluid channel bottom and the first chamber bottom ensures that hydrogel filled into the chamber does not flow over into the fluid channel as long as the volume of hydrogel filled into the chamber is not greater than the chamber volume. Preferably, the filled hydrogel volume is at least 5%, more preferably at least 10%, more preferably at least 20%, more preferably at least 30%, less than the chamber volume.

According to a preferred embodiment of the present invention, the height difference between the fluid channel bottom and the first chamber bottom is at least 0.1 mm, preferably at least 0.2 mm, more preferably at least 0.25 mm, more preferably at least 0.4 mm.

According to a particularly preferred embodiment of the present invention, the ratio of the height difference between the fluid channel bottom and the first chamber bottom and the height of the main chamber is 1:5 to 1:15, preferably 1:5 to 1:12, more preferably 1:5 to 1:10, more preferably 1:6 to 1:10, more preferably 1:7 to 1:9, in particular 1:8. It has been shown that at such height ratios, the hydrogel introduced into the main chamber is not flushed out of the main chamber by a fluid stream in the fluid channel.

According to another preferred embodiment of the present invention, the height of the fluid channel extends from the fluid channel bottom to the ceiling of the main chamber and is preferably in contact therewith over the entire height.

Preferably, the secondary chamber has a smaller volume than the main chamber. As a result of this, a larger mass fraction of the cell culture is formed in the main chamber, and the secondary chamber is used for anchoring the cell culture. As a result of this, the portion of the cell culture located in the main chamber can be used for experiments and studies.

According to the preferred embodiment, the loading opening is connected to the secondary chamber. This ensures that the hydrogel first fills the secondary chamber before flowing into to the main chamber. As a result of this, the advantage is achieved that it is ensured that the secondary chamber is also filled with hydrogel when the main chamber is being filled.

Preferably, the secondary chamber is connected to the main chamber at a side of the main chamber opposite the fluid channel. This ensures that the hydrogel does not flow directly from the loading opening via the secondary chamber into the fluid channel during filling of the chamber.

According to a preferred embodiment of the present invention, a semipermeable membrane, preferably a silicone membrane, delimiting the fluid channel is arranged in the main chamber. The semipermeable membrane can be an additional barrier against flushing out of the cell culture/organoid or hydrogel arranged in the main chamber.

According to one embodiment variant of the device according to the invention, the device comprises a conduit connecting the loading opening to the chamber. As a result of this, the advantage is achieved that the hydrogel can be loaded into the chamber in a reproducible manner, thereby achieving a reproducible distribution of the hydrogel in the chamber.

Preferably, the main chamber has a space diagonal which is from 2 to 20 mm, preferably from 2 to 15 mm, more preferably from 3 to 10 mm, more preferably from 4 to 6 mm.

Expediently, the fluid channel bottom also has a distance from the first chamber bottom of 0.1 to 10 mm, preferably from 0.2 to 5 mm, more preferably from 0.2 to 2 mm, more preferably from 0.2 to 1 mm, more preferably from 0.2 to 0.4 mm.

According to the preferred embodiment, the chamber, the main chamber, the secondary chamber and/or the fluid channel comprise an antifouling surface coating, preferably selected from the group consisting of a polyethylene glycol (PEG)-based polymer, a polysaccharide, in particular agarose, a polyhydroxy polymer, in particular poly(2-hydroxy-ethyl methacrylate) (poly-HEMA), 2-methacryloyloxyethyl phosphorylcholine (MPC), dextran or hydroxyethyl cellulose (HEC), a natural polymer, in particular an S-layer protein, and combinations thereof. This prevents fouling of these components by cells located therein so that biofilm formation does not occur.

The carrier according to the invention comprises at least one microfluidic device according to the invention. As a result of this, the advantage is achieved that one or more devices according to the invention can be produced or provided together on one carrier.

Preferred embodiments as well as alternative embodiment variants of the device according to the invention, of the carrier according to the invention and of the method according to the invention are explained in more detail in the following with reference to the figures.

Figure 2:
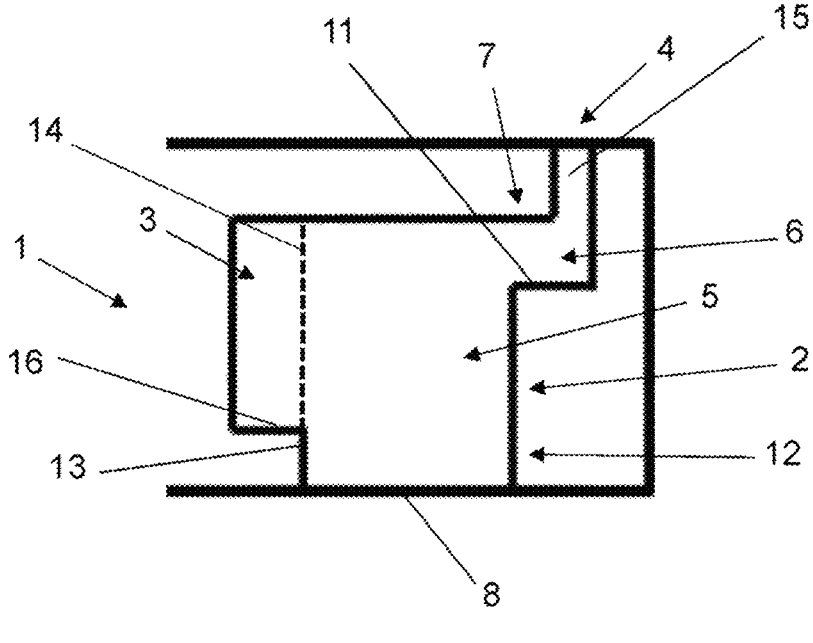
FIG. 2 shows a side view of the microfluidic device of FIG. 1.
Figures 5A, 5B, 5C, 6A, 6B, 6C:
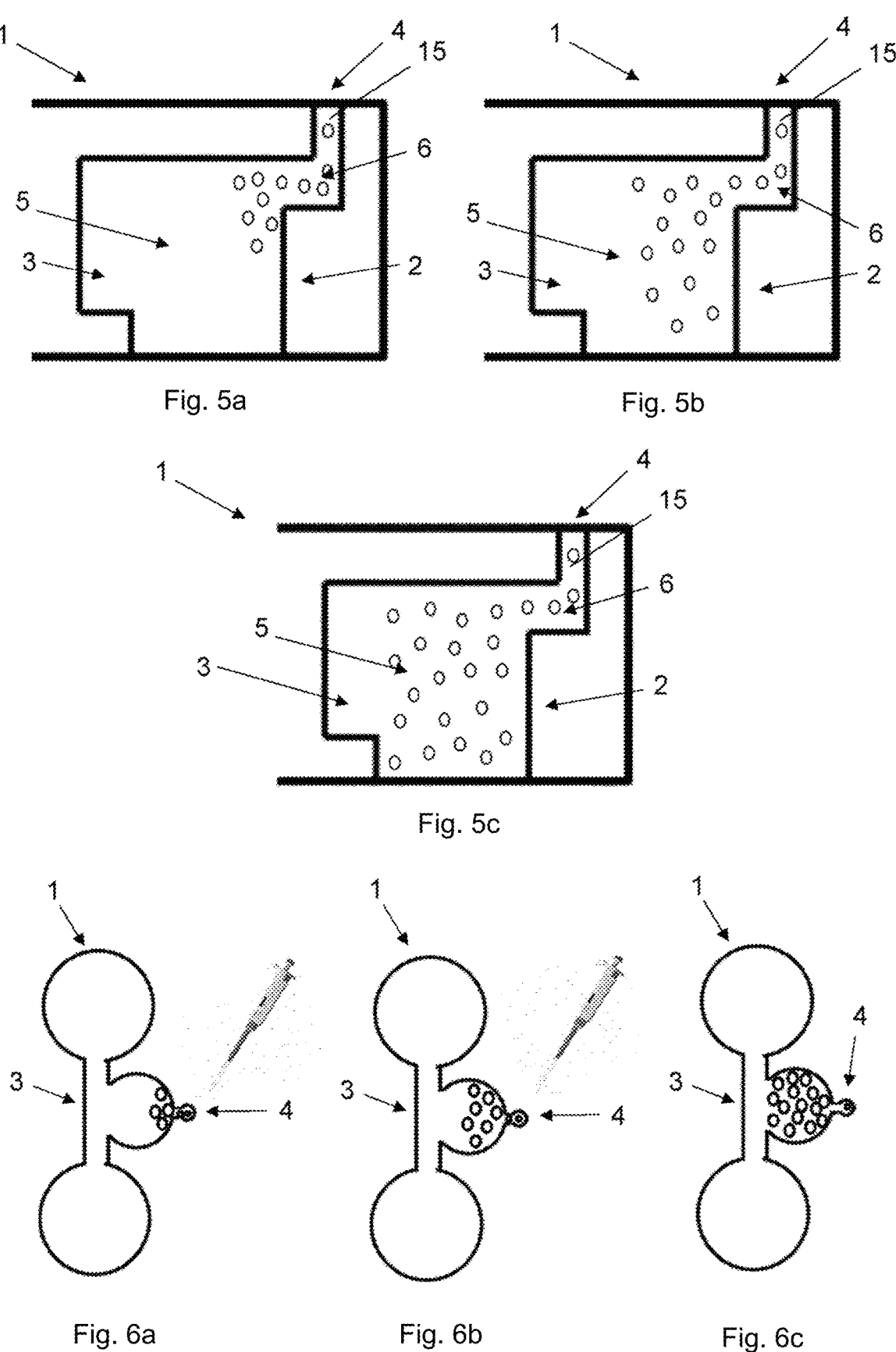
FIG. 5a, FIG. 5b and FIG. 5c show the microfluidic device illustrated in FIG. 2 during loading of the device with hydrogel.
FIG. 6a, FIG. 6b, and FIG. 6c show a top view of the microfluidic device during loading with hydrogel.

FIG. 1 shows a microfluidic device 1 according to the invention, preferably for producing a three-dimensional cell culture, in a top view with at least one chamber 2 and a fluid channel 3 extending at least partially through the chamber 2. In the preferred embodiment of the device 1 according to the invention illustrated in FIG. 1, the device has a chamber 2 through which the fluid channel extends in an edge region of the chamber 2. The fluid channel 3 is designed to provide a fluid stream preferably continuously passing through the chamber 2. The chamber 2 is connected to a loading opening 4 and can be loaded with hydrogel via the loading opening 4 up to a desired fill level. Loading with hydrogel is illustrated in FIGS. 5a, 5b and 5c and will be discussed further below. The chamber 2 has a main chamber 5 and a secondary chamber 6 connected to the main chamber 5. The main chamber 5 and the secondary chamber 6 are shown in FIG. 1 and in FIG. 2, wherein FIG. 2 is a side view of the microfluidic device 1 illustrated in FIG. 1. The secondary chamber 6 can be at least partially filled with hydrogel when the chamber 2 is being loaded with hydrogel up to the desired fill level. By dividing the chamber 2 into the main chamber 5 and the secondary chamber 6 in conjunction with the fact that when the main chamber 5 is filled with hydrogel to the desired fill level, the secondary chamber 6 is also at least partially filled with hydrogel, the advantage is achieved that during the formation of the three-dimensional cell culture, a portion of the cell culture forms in the secondary chamber 6. This means that the secondary chamber 6 is designed or constructed to be at least partially filled with hydrogel backed up from the main chamber 5 when the chamber 2 is being loaded with hydrogel to the desired fill level. By means of this portion located in the secondary chamber 6, the entire cell culture is fixed in the chamber 2, thus preventing the cell culture from slipping in the chamber 2. As a result of this, the reproducibility of tests and experiments on the cell culture carried out with different cell cultures produced in a plurality of devices 1 according to the invention is improved.

As can be seen in FIG. 1 and FIG. 2, according to the preferred embodiment of the device 1 according to the invention, the main chamber 5 and the secondary chamber 6 are connected by a connecting channel 7, wherein the connecting channel 7 has a smaller cross section than the main chamber 5 and the secondary chamber 6. As a result of this, the advantage is achieved that the cell culture is fixed even stronger by the cross-sectional constriction between the main chamber 5 and the secondary chamber 6, and the position of the cell culture is precisely defined.

As can be seen in FIG. 2, according to the preferred embodiment of the device 1 according to the invention, the fluid channel 3 extends at least partially through the main chamber 5, and the main chamber 5 comprises a first chamber bottom 8. The fluid channel 3 also comprises a fluid inlet 9 arranged spaced apart from the first chamber bottom 8 in the main chamber 5, as well as a fluid outlet 10 arranged spaced apart from the first chamber bottom 8 in the main chamber 5. The arrangement of fluid inlet 9 and fluid outlet 10 can be seen in FIG. 1. As a result of this, the advantage is achieved that between the main chamber 5 and the fluid inlet 9 and the fluid outlet 10, respectively, a step is formed which prevents hydrogel from flowing into the fluid inlet 9 and the fluid outlet 10, respectively, during loading of the chamber 2.

Preferably, as shown in FIG. 2, the main chamber 5 has a first chamber bottom 8 and the secondary chamber 6 has a second chamber bottom 11. Preferably, the first chamber bottom 8 is formed at a lower height level than the second chamber bottom 11. As a result of this, the advantage is achieved that the majority of the hydrogel accumulates in the main chamber 5, and the secondary chamber 6 provides an anchorage for a cell culture mostly produced or grown in the main chamber 5.

Expediently, the fluid channel 3 has a fluid channel bottom 16 shown in FIG. 2, wherein the fluid channel bottom 16 is formed at a higher height level than the first chamber bottom 8. This prevents hydrogel from flowing into the fluid channel 3 during loading of the chamber 2.

Furthermore, it can be seen in FIG. 2 that according to the preferred embodiment of the device 1 according to the invention, the fluid channel bottom 16 is formed at a lower height level than the second chamber bottom 11. As a result of this, a reservoir for hydrogel in which the cell culture can grow is formed in the main chamber 5.

In addition, the secondary chamber 6 according to the preferred embodiment shown in the figures has a smaller volume than the main chamber 5. As a result of this, a larger mass fraction of the cell culture is formed in the main chamber 5, and the secondary chamber 6 is used for anchoring the cell culture. Thus, the portion of the cell culture located in the main chamber 5 can be used for experiments and studies.

In addition, in this embodiment, the loading opening 14 is connected to the secondary chamber 6, as shown in FIG. 2. This ensures that the hydrogel first fills the secondary chamber 6 before flowing into the main chamber 5. As a result of this, the advantage is achieved that it is ensured that the secondary chamber 6 is also filled with hydrogel when the main chamber 5 is being filled.

Preferably, the secondary chamber 6 is connected to the main chamber 5 at a side 12 of the main chamber 5 opposite the fluid channel. This ensures that the hydrogel does not flow directly from the loading opening 4 via the secondary chamber 6 into the fluid channel 3 during filling of the chamber 2.

Expediently, a semi-permeable membrane 14 delimiting the fluid channel 3 is arranged in the main chamber 5. The silicone membrane 14 is shown in FIG. 2 with a dashed line. The semipermeable membrane 14 forms a barrier against the cell culture or hydrogel arranged in the main chamber 5 being flushed out by the fluid stream in the fluid channel 3.

According to one embodiment variant of the device 1 according to the invention, the device 1 comprises a conduit 15 connecting the loading opening 4 to the chamber 2. This can be seen in FIG. 2. As a result of this, the advantage is achieved that the hydrogel can be filled into the chamber 2 in a reproducible manner, whereby a reproducible distribution of the hydrogel in the chamber 2 is achieved.

Preferably, the main chamber 5 has a space diagonal which is from 2 to 20 mm, preferably from 2 to 15 mm, more preferably from 3 to 10 mm, more preferably from 4 to 6 mm.

Expediently, the fluid channel bottom 16 further has a distance from the first chamber bottom 8 of 0.1 to 10 mm, preferably of 0.2 to 5 mm, more preferably of 0.2 to 2 mm, more preferably of 0.2 to 1 mm, more preferably of 0.2 to 0.4 mm.

According to the preferred embodiment, the chamber 2, the main chamber 5, the secondary chamber 6 and/or the fluid channel 3 comprise an antifouling surface coating which is not shown in the figures, this coating preferably being selected from the group consisting of a polyethylene glycol (PEG)-based polymer, a polysaccharide, in particular agarose, a polyhydroxy polymer, in particular poly(2-hydroxyethyl methacrylate) (poly-HEMA), 2-methacryloyloxyethyl phosphorylcholine (MPC), dextran or hydroxyethyl cellulose (HEC), a natural polymer, in particular an S-layer protein and combinations thereof and/or an antifouling material based on fluorinated silanes or phosphatidylcholine coatings. This prevents unwanted fouling of these components by cells.

Figure 3:
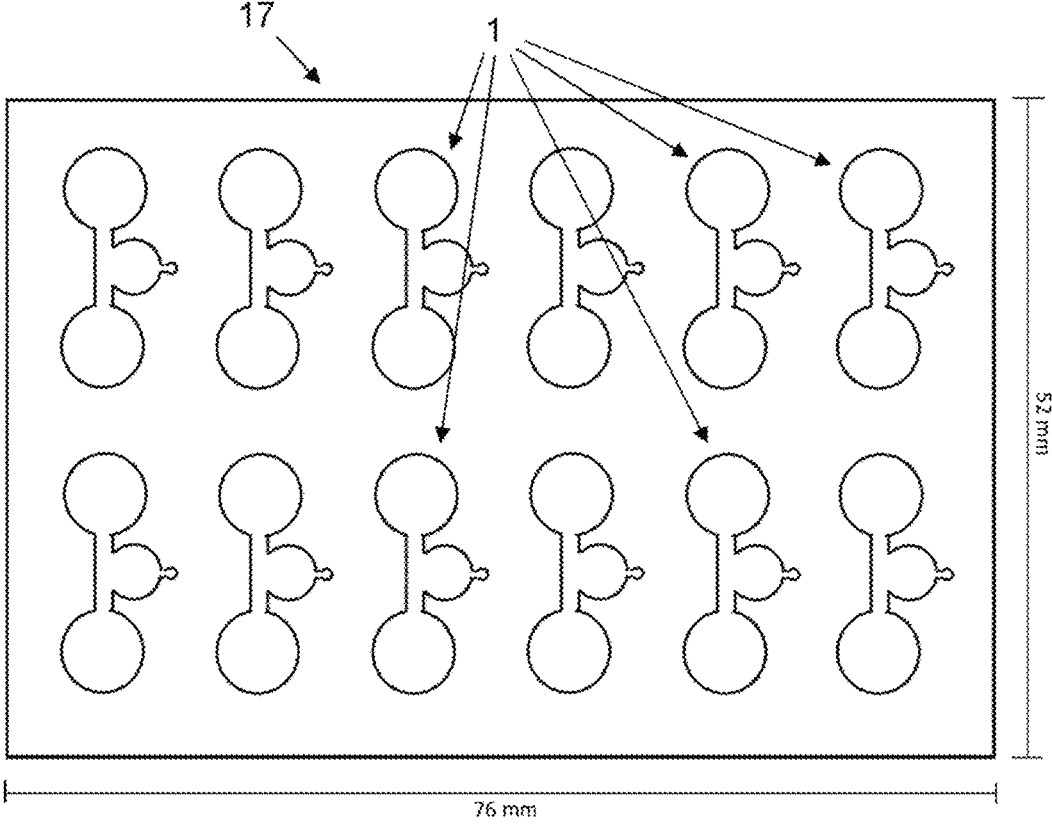
FIG. 3 shows a top view of a carrier with twelve microfluidic devices according to the invention.
Figure 4:
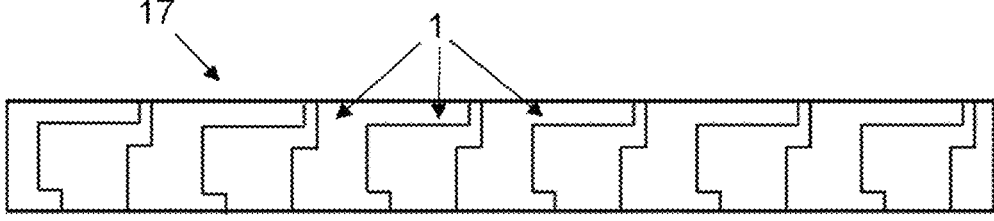
FIG. 4 shows a side view of the carrier illustrated in FIG. 3.

FIG. 3 shows a carrier 17 according to the invention which comprises at least one microfluidic device 1 according to the invention. The carrier 17 illustrated in FIG. 3 comprises 12 microfluidic devices 1 according to the invention. As a result of this, the advantage is achieved that one or more devices 1 according to the invention can be produced or provided together on one carrier 17. The carrier 17 shown as an example in FIG. 3 has dimensions of 76 mm by 52 mm. FIG. 4 shows a side view of the carrier 17 of FIG. 3.

FIG. 5a, FIG. 5b and FIG. 5c show the gradual loading of the device 1 according to the invention with hydrogel and the spreading of the hydrogel in the device 1 in the course of the loading. The hydrogel is symbolized with small spheres. It spreads through the loading opening 4 via the secondary chamber 6 into the main chamber 5.

FIG. 6a, FIG. 6b and FIG. 6c show the spreading shown in FIGS. 5a, 5b and 5c in a top view, with a syringe used for introducing the hydrogel into the loading opening 4.

Figure 7:
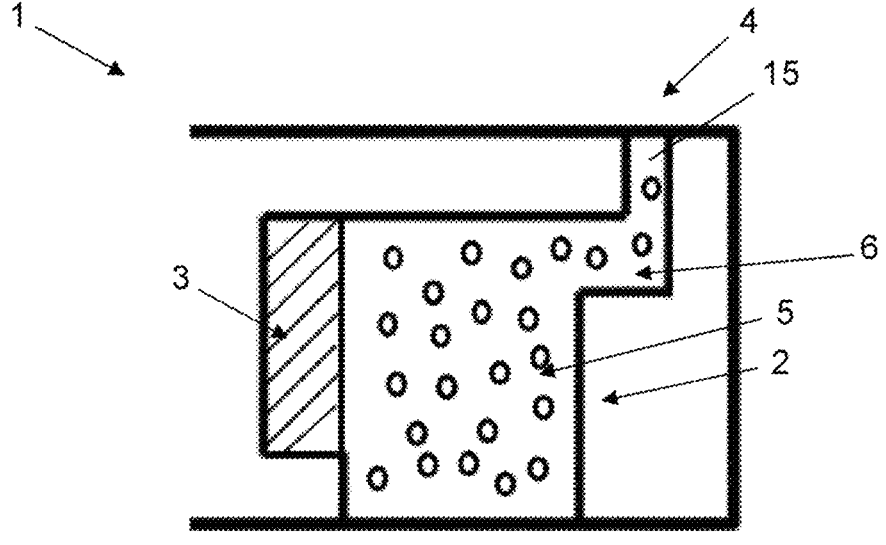
FIG. 7 shows a side view of the microfluidic device after loading with hydrogel with a fluid channel.
Figures 8A, 8B, 8C, 9A, 9B, 9C:
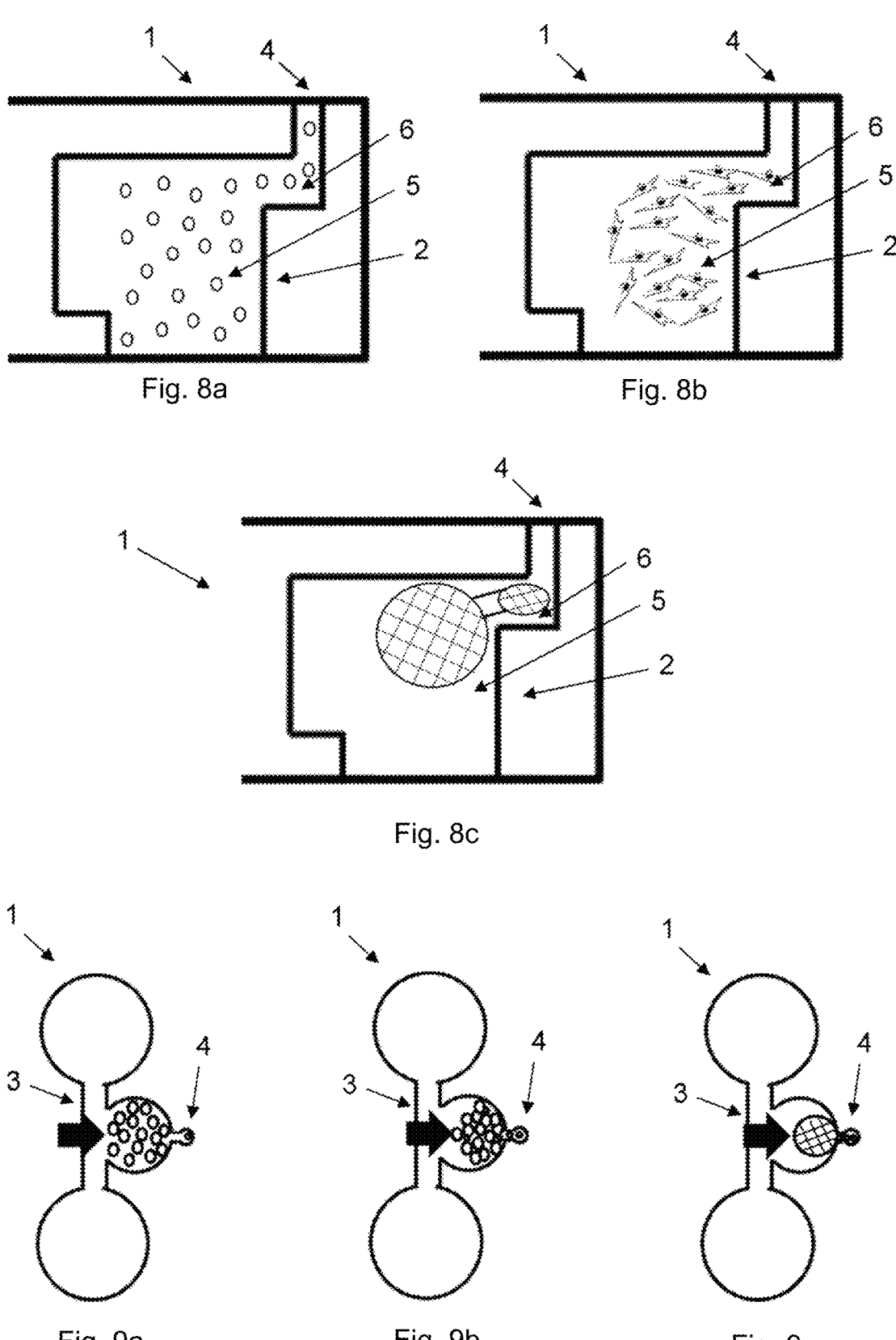
FIG. 8a, FIG. 8b, and FIG. 8c show a side view of the microfluidic device according to the invention during the formation of a three-dimensional cell culture.
FIG. 9a, FIG. 9b and FIG. 9c show a side view of the microfluidic device of FIG. 8a, FIG. 8b and FIG. 8c.

FIG. 7 shows the device 1 according to the invention in a state loaded with hydrogel, the fluid channel 3 being marked with a shaded area and being free of hydrogel.

Another aspect of the present invention relates to a method for producing a three-dimensional cell culture or organoid with a microfluidic device according to the present invention, comprising a step (A) of loading a chamber of the device according to the invention through a loading opening with hydrogel up to a desired fill level.

In a first step (A) of the method according to the present invention, hydrogel is introduced into the chamber. In the course of this, as much hydrogel is filled into the chamber as is necessary to cause a backpressure of the hydrogel up to the secondary chamber. In such a case, it is ensured that the contracting hydrogel or cell/hydrogel mixture remains fixed to the secondary chamber of the main chamber.

According to a preferred embodiment of the present invention, cells are introduced together into the chamber (2) in and/or before step (A) through a loading opening and/or via a fluid inlet (9).

In the method according to the present invention, the cells can be applied into the chamber after and/or before step (A) (introduction of hydrogel into the chamber of the device according to the invention). Alternatively, it is also possible to introduce the cells into the chamber together with the hydrogel.

According to another preferred embodiment of the present invention, the cells are selected from stem cells and primary cells, preferably fibroblasts, cartilage cells, endothelial cells, epithelial cells, fat cells, induced pluripotent stem cells (IPS), osteoclasts, osteoblasts or osteocytes.

Cells, in particular animal or human cells, of various origins can be introduced into the device according to the invention, provided that they are capable of forming a three-dimensional structure (such as an organoid). For example, if stem cells are introduced into the device, they can be differentiated directly in the device according to known methods.

The cultivation medium introduced into the chamber through the fluid channel is selected according to the cells used. Corresponding media are sufficiently known to the person skilled in the art.

According to a preferred embodiment of the present invention, the hydrogel comprises or consists of Matrigel®, fibrin, collagen, PEG-based hydrogel, gelatin-based hydrogel, hyaluronic acid-based hydrogel, alginate-based hydrogel, silk-based hydrogel, and combinations thereof.

The hydrogel preferably has a concentration of from 0.1 mg/ml to 500 mg/ml, more preferably from 0.5 mg/ml to 500 mg/ml.

According to a preferred embodiment of the present invention, the device according to the invention is incubated after step (A) for 12 hours to 60 days, preferably for 1 to 30 days, more preferably for 2 to 20 days.

In order to produce organoids or three-dimensional cell cultures, it is advantageous to incubate the device comprising the cells and the hydrogel for a certain period of time at conditions that allow the cells to grow.

According to a particularly preferred embodiment of the present invention, the device according to the invention is incubated at a temperature of from 25 to 38° C., preferably from 37 to 38° C.

The temperature at which the device according to the invention is incubated depends on the cells to be cultured and is preferably varied in a range from 25 to 38° C.

According to another preferred embodiment of the present invention, after step (A), in a step (B), the chamber is supplied with a fluid stream continuously or discontinuously passing through a fluid channel, wherein in the case of a discontinuous fluid stream, the fluid is preferably changed.

During the cultivation of cells within the device according to the invention, the fluid stream in the fluid channel can be continuous or discontinuous (i.e., with interruptions or changed flow rate). In addition, it is possible to change the composition of the fluid (e.g., nutrient medium) flowing through the fluid channel over time or during cultivation of the cells. On the one hand, this allows natural processes to be simulated since the supply of nutrients or a fluid stream "washing around" tissue also changes or can change in the human or animal body. Changing the flow rate and composition of the fluid in the fluid channel also has the advantage that the influence of fluid streams and substances on cell growth or the state of the cells within the device according to the invention can be investigated.

According to a preferred embodiment of the present invention, the $CO_2$ and/or $O_2$ content and/or pH within the device and/or fluid stream is controlled.

In order to observe the growth of the cells and their condition within the device according to the invention, it is advantageous to record and monitor certain parameters, in particular the above-mentioned parameters, in order to take appropriate measures if necessary.

Yet another aspect of the present invention relates to a method for determining the influence of a chemical compound and/or at least one physical parameter on cells of a three-dimensional cell culture in a microfluidic device according to the invention, comprising the steps of:

a) detecting a first state of the cells, b1) contacting the cells with a chemical compound and/or b2) changing a physical parameter within the microfluidic device, c) detecting a second state of the cells, and d) determining the influence of the chemical compound and/or the at least one physical parameter on the cells by identifying a difference between the first state and second state of the cells.

With the device according to the invention it is possible to determine the influence of physical parameters or substances or substance mixtures on three-dimensional cell cultures or organoids. In the process of this, it is to be detected first in which state the cells are before the addition of a substance or a mixture of substances, or before the physical parameters are changed. Detecting the state of the cells can be done using different methods. On the one hand, it is possible to determine whether the cell culture or the organoid releases certain substances (e.g. chemokines). On the other hand, it is also possible to use purely optical methods, wherein the optical state of the culture or organoid is observed. The same examinations are performed after step b1) and/or b2) to detect a second state. From the difference between the first and second states, the influence of a physical parameter or a substance or a substance mixture on the cells can be derived.

The influence of the chemical compound and/or the at least one physical parameter on the cells can preferably be determined by measuring viability, morphology, secretion of substances from the cells, optical transparency and/or opacity, or combinations thereof.

Such methods are mentioned, for example, in Kratz SRA et al. (Biosensors 2019, 9 (3), 110).

According to a preferred embodiment of the present invention, the influence of the chemical compound and/or the at least one physical parameter on the cells is determined by measuring the release of biomolecules, in particular antibodies, chemokines, cytokines, enzymes, or microRNA Particularly preferably, the amounts or concentration of interleukins, matrix metalloproteinases, growth factors such as BMP, EGF; VEGF, FGF, BAFF, etc. are determined (see, e.g., Rothbauer M et al. (Lab Chip, 2018, 18, 249-270)).

According to a preferred embodiment of the present invention, the physical parameter is selected from the group consisting of temperature and pH.

The present invention is explained in more detail with reference to, but not limited to, the following embodiments and examples.

EMBODIMENTS

1. A microfluidic device (1), preferably for producing a three-dimensional cell culture, with at least one chamber (2) and a fluid channel (3) extending at least partially through the chamber (2) for providing a fluid stream preferably continuously passing through the chamber (2), wherein the chamber (2) is connected to a loading opening (4) and can be loaded with hydrogel via the loading opening (4) up to a desired fill level, characterized in that the chamber (2) comprises a main chamber (5) and a secondary chamber (6) connected to the main chamber (5), wherein, when the chamber (2) is being loaded with hydrogel up to the desired fill level, the secondary chamber (6) can be at least partially filled with hydrogel.

2. The device (1) according to embodiment 1, characterized in that the main chamber (5) and the secondary chamber (6) are connected by a connecting channel (7), wherein the connecting channel (7) has a smaller cross section than the main chamber (5) and the secondary chamber (6).

3. The device (1) according to any one of embodiments 1 or 2, characterized in that the fluid channel (3) extends at least partially through the main chamber (5), and the main chamber (5) has a first chamber bottom (8), wherein the fluid channel (3) comprises a fluid inlet (9) arranged spaced apart from the first chamber bottom (8) in the main chamber (5) as well as a fluid outlet (10) arranged spaced apart from the first chamber bottom (8) in the main chamber (5).

4. The device (1) according to any one of embodiments 1 to 3, characterized in that the main chamber (5) has a first chamber bottom (8) and the secondary chamber (6) has a second chamber bottom (11), wherein the first chamber bottom (8) is formed at a lower height level than the second chamber bottom (11).

5. The device (1) according to embodiment 3 or 4, characterized in that the fluid channel (3) comprises a fluid channel bottom (16), wherein the fluid channel bottom (16) is formed at a higher height level than the first chamber bottom (8).

6. The device (1) according to embodiment 5, characterized in that the fluid channel bottom (16) is formed at a lower height level than the second chamber bottom (11).

7. The device (1) according to any one of embodiments 1 to 6, characterized in that the secondary chamber (6) has a smaller volume than the main chamber (5).

8. The device (1) according to any one of embodiments 1 to 7, characterized in that the loading opening (4) is connected to the secondary chamber (6).

9. The device (1) according to any one of the embodiments 1 to 8, characterized in that the secondary chamber (6) is connected to the main chamber (5) on a side (12) of the main chamber (5) opposite the fluid channel (3).

10. The device (1) according to any one of embodiments 1 to 9, characterized in that the fluid channel (3) runs along a side wall (13) of the main chamber (5).

11. The device (1) according to any one of embodiments 1 to 10, characterized in that a semipermeable membrane (14), preferably a silicone membrane, delimiting the fluid channel (3) is arranged in the main chamber (5).

12. The device (1) according to any one of embodiments 1 to 11, characterized in that the device (1) comprises a conduit (15) connecting the loading opening (4) to the chamber (2).

13. The device (1) according to any one of embodiments 1 to 12, characterized in that the main chamber (5) has a space diagonal which is 2 to 20 mm, preferably 2 to 15 mm, more preferably 3 to 10 mm, more preferably 4 to 6 mm.

14. The device (1) according to any one of embodiments 5 to 13, characterized in that the fluid channel bottom (16) has a distance from the first chamber bottom (8) of 0.1 to 10 mm, preferably of 0.2 to 5 mm, more preferably of 0.2 to 2 mm, more preferably of 0.2 to 1 mm, more preferably of 0.2 to 0.4 mm.

15. The device (1) according to any one of embodiments 1 to 14, characterized in that the chamber (2), the main chamber (5), the secondary chamber (6) and/or the fluid channel (3) comprise an antifouling surface coating, preferably selected from the group consisting of a polyethylene glycol (PEG)-based polymer, a polysaccharide, in particular agarose, a polyhydroxy polymer, in particular poly(2-hydroxyethyl methacrylate) (poly-HEMA), 2-methacryloyloxyethyl phosphorylcholine (MPC), dextran or hydroxyethyl cellulose (HEC), a natural polymer, in particular an S-layer protein, and combinations thereof.

16. A carrier (17), comprising at least one microfluidic device according to any one of claims 1 to 15.

17. A method for producing a three-dimensional cell culture or organoid with a microfluidic device (1) according to any one of claims 1 to 15, comprising a step (A) of loading a chamber (2) of the device (1) through a loading opening (4) with hydrogel up to a desired fill level.

18. The method according to embodiment 17, characterized in that cells are introduced together in and/or before step (A) through a loading opening (4) and/or via a fluid inlet (9) into the chamber (2).

19. The method according to embodiment 18, characterized in that the cells are selected from stem cells and primary cells, preferably fibroblasts, cartilage cells, endothelial cells, epithelial cells, fat cells, induced pluripotent stem cells (IPS), osteoclasts, osteoblasts or osteocytes.

20. The method according to any one of embodiments 17 to 19, characterized in that the hydrogel comprises or consists of Matrigel®, fibrin, collagen, PEG-based hydrogel, gelatin-based hydrogel, hyaluronic acid-based hydrogel, alginate-based hydrogel, silk-based hydrogel, and combinations thereof.

21. The method according to any one of embodiments 17 to 20, characterized in that after step (A), the device (1) is incubated for 12 hours to 60 days, preferably for 1 to 30 days, more preferably for 2 to 20 days.

22. The method according to embodiment 21, characterized in that the device (1) is incubated at a temperature of from 25 to 38° C., preferably from 37 to 38° C.

23. The method according to any one of embodiments 17 to 22, characterized in that after step (A), in a step (B), the chamber (2) is supplied with a fluid stream continuously or discontinuously passing through a fluid channel (3), wherein in the case of a discontinuous fluid stream, the fluid is preferably changed.

24. The method according to any one of embodiments 17 to 23, characterized in that the $CO_2$ and/or $O_2$ content and/or the pH within the device and/or the fluid stream is controlled.

25. A method for determining the influence of a chemical compound and/or at least one physical parameter on cells of a three-dimensional cell culture in a microfluidic device according to any one of claims 1 to 16, comprising the steps of:
a) detecting a first state of the cells,
b1) contacting the cells with a chemical compound and/or
b2) changing a physical parameter within the microfluidic device,
c) detecting a second state of the cells, and d) determining the influence of the chemical compound and/or the at least one physical parameter on the cells by identifying a difference between the first state and second state of the cells.

26. The method according to embodiment 25, characterized in that the influence of the chemical compound and/or the at least one physical parameter on the cells is determined by measuring viability, morphology, secretion of substances from the cells, optical transparency and/or opacity, or combinations thereof 27. The method according to embodiment 25 or 26, characterized in that the influence of the chemical compound and/or the at least one physical parameter on the cells is determined by measuring the release of biomolecules, in particular antibodies, chemokines, cytokines, enzymes or microRNA 28. The method according to any one of embodiments 25 to 27, characterized in that the physical parameter is selected from the group consisting of temperature and pH.

EXAMPLES

Example 1: Characterization of the Condensation Behavior of Synovial Fibroblasts Methods Chip Production To clean the base of the chip, a microscope slide (76×26 mm) from VWR was first placed in a 2% Hellmanex® III solution and treated in the ultrasonic bath for 5 minutes. Thereafter, the solution was discarded and the procedure was repeated first with isopropanol and then with water. Finally, the microscope slides were dried with compressed air and in an oven for 1 hour at 80° C.

For chip production, 5 PDMS layers (76×26 mm) had to be cut out first. For this purpose, 0.5 mm thick PDMS film was inserted into the Roland DG CAMM-1 GS-24 cutter and the desired shape was cut out, which was removed with tweezers. Then, the individual layers were bonded together by plasma activation, starting with the microscope slide and the first layer of PDMS film. The strength of the bond was enhanced by heat treatment in an oven (80° C.).

Prior to using the chip, all chambers, channels and reservoirs were purged with 70% ethanol. The cell chambers were also coated with Lipidure®, an antifouling agent. Finally, the chip was sterilized with UV light.

Cell Culture

Synovial fibroblasts were cultured with culture medium (DMEM, 10% FBS, 1% antibiotic, 1% MEM NEAA) in culture flasks (37° C., 5% $CO_2$) and detached from the flask at 90% confluence. For this purpose, cells were incubated with 1× trypsin solution at 37° C. for 5 minutes and then medium was added to stop the reaction. The cell suspension was counted by means of trypan blue and centrifuged (4° C., 1400 rpm, 5 min). Subsequently, the cell pellet was resuspended in medium and the required amount of cells was separated. After recentrifugation, the cell pellet was mixed with Matrigel® 3000 cells per µl Matrigel®) and the chips were filled with 45 µl cell/Matrigel® suspension per cell chamber. After 40 min of polymerization at 37° C., 3D cultivation medium was added (DMEM, 10% FBS, 1% antibiotic, 1% MEM NEAA, 1% ITS, 31.6 µg/ml L-ascorbic acid 2-phosphate, 2% HEPES). Chips were cultured at 37° C. and 5% $CO_2$ for up to 4 weeks and the medium was exchanged twice a week.

Results and Discussion

Figure 10:
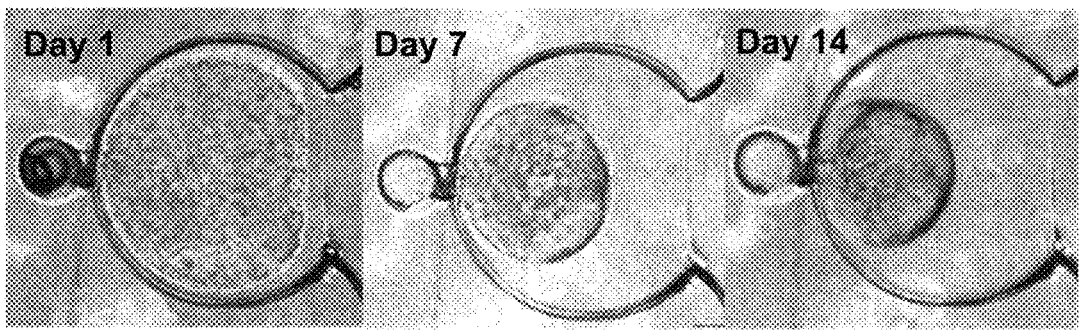
FIG. 10 shows a top view of a microfluidic device according to the invention while primary human synovial fibroblasts remodel the hydrogel to become a micromass with physiological structures over the course of fourteen days.
Figure 11:
FIG. 11 shows a change in micromass structure of primary human synovial fibroblasts embedded in hydrogel.
Figure 11:
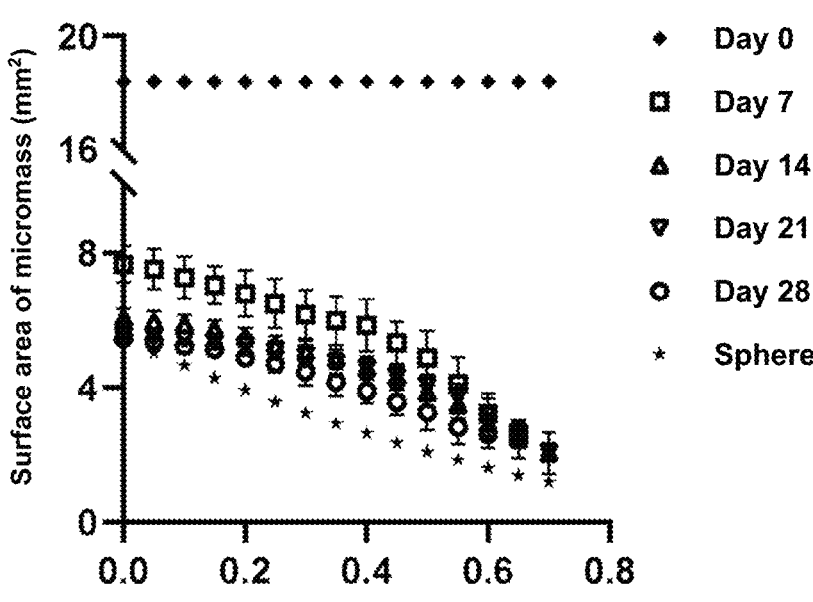
Figure 12:
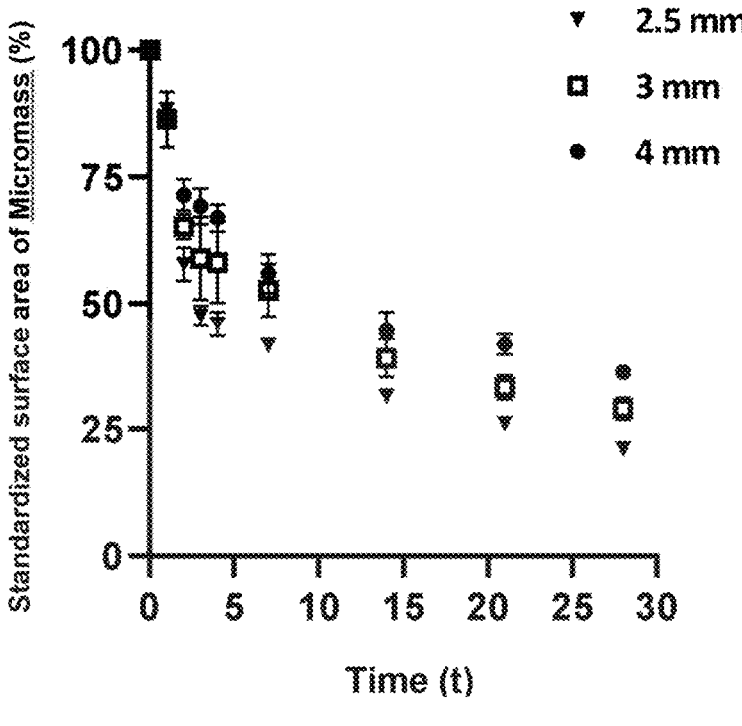
FIG. 12 shows a progression of micromass condensation of primary human synovial fibroblasts embedded in hydrogel at different cell chamber heights.
Figure 13:
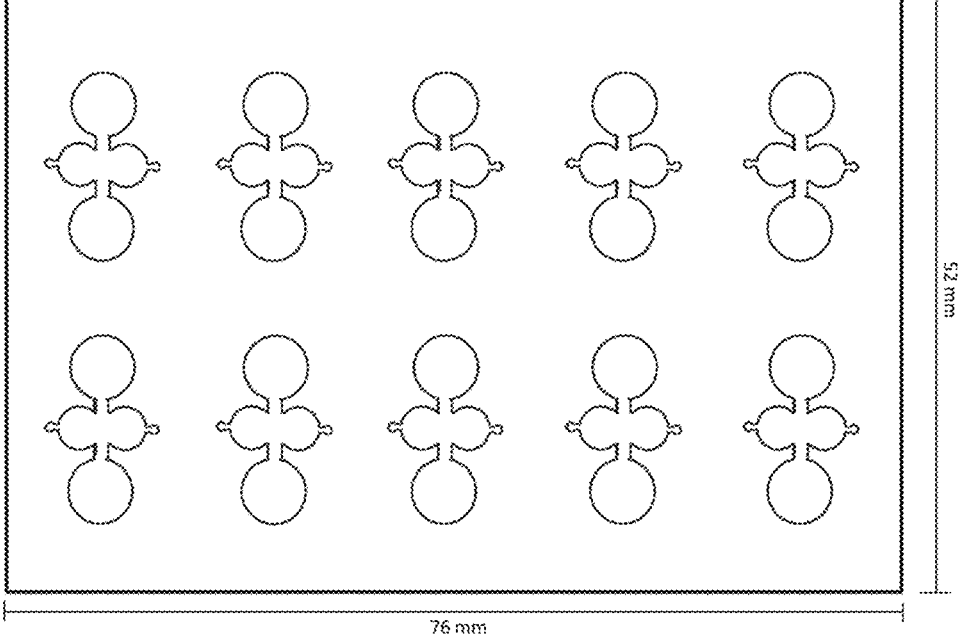
FIG. 13 shows a top view of a carrier with eight microfluidic devices for a co-culture according to the invention.

The synovial fibroblasts enter into cell-cell junctions and begin to release their own extracellular matrix. The Matrigel® in which the cells are initially located is remodeled and, due to the strong cell-cell junctions, the so-called micromass condenses over time (FIG. 10). The condensation takes place in a controlled manner back towards the loading opening since remaining cells in the loading channel form a miniaturized micromass. The latter cannot enter the actual cell chamber because the inlet channel is narrowed. The miniaturized micromass is connected to the large micromass in the cell chamber by cells. During the remodeling of the Matrigel® and the condensation, a micromass similar to synovial tissue is formed. Characteristic of synovial tissue is a denser layer of cells towards the medium and a rather loose tissue inside the micromass. Condensation changes the structure since initially, the cell/Matrigel® suspension polymerizes in a cylinder-like chamber. As it contracts, a spherical micromass is formed. To verify this assumption, phase contrast images of the micromass were taken at regular intervals along the z-axis. Based on the plane of focus, the size of the cross section could be determined at different positions. FIG. 11 shows that the shape changes only slightly after 14 days. However, a comparison with a sphere shows that the curve should be somewhat different. Therefore, the assumption is that the micromass is ellipsoidal in shape since the diameter of the chamber is 2.5 times the height. To weigh the influence of height on condensation, chips were built with cell chambers of different heights. FIG. 12 shows that no significant changes in condensation behavior are observed. Differences are mainly based on the difference in volume.

Example 2: Condensation Behavior of Synovial Fibroblasts in the Presence of Immune Cells Methods
Chip Production To clean the base of the chip, a microscope slide (76×26 mm) of VWR, was first placed in a 2% Hellmanex® III solution and treated in the ultrasonic bath for 5 minutes. The solution was then discarded and the procedure was repeated first with isopropanol and then with water. Finally, the microscope slides were dried with compressed air and in an oven for 1 hour at 80° C.

For chip fabrication, 5 PDMS layers (76×26 mm) had to be cut out first. For this purpose, 0.5 mm thick PDMS film was inserted into the Roland DG CAMM-1 GS-24 cutter and the desired shape was cut out, which was removed with tweezers. Then, the individual layers were bonded together by plasma activation, starting with the microscope slide and the first layer of PDMS film. The strength of the bond was enhanced by heat treatment in an oven (80° C.).

Figure 14:
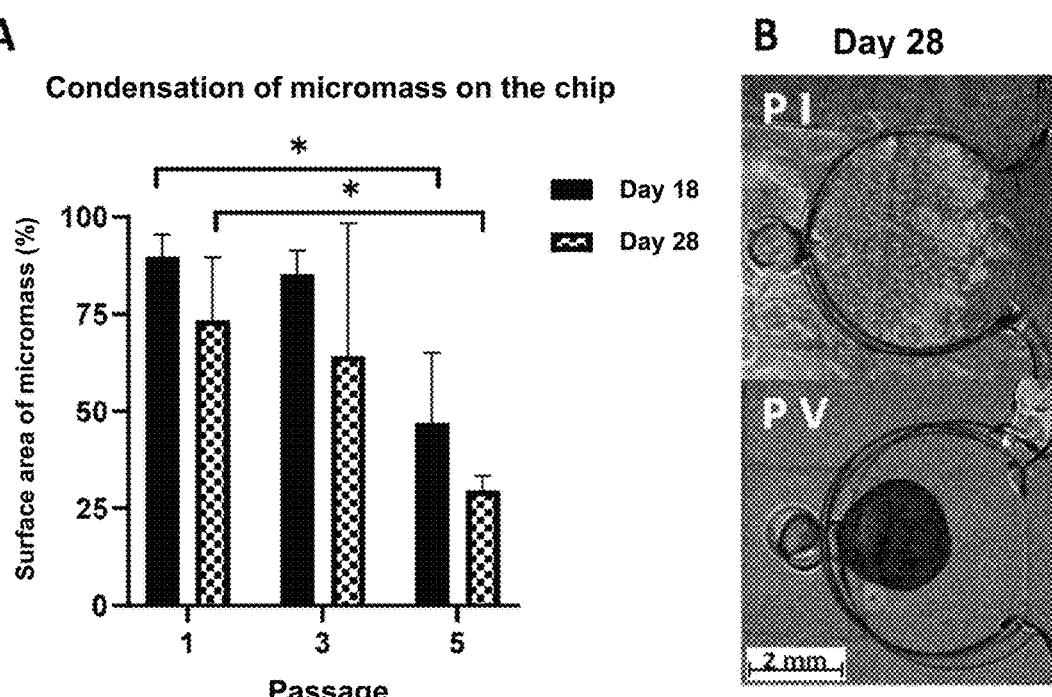
FIG. 14A and FIG. 14B show the condensation of micromasses in the device according to the invention as a function of the passage of human synovial fibroblasts.

Prior to using the chip, all chambers, channels and reservoirs were purged with 70% ethanol. The cell chambers were also coated with Lipidure®, an antifouling agent. Finally, the chip was sterilized with UV light.
Cell Culture Cell suspensions of surgical specimens were thawed and cultured (37° C., 5% $CO_2$) with culture medium (DMEM, 10% FBS, 1% antibiotic, 1% MEM NEAA) in culture flasks. At 90% confluence, the cells were detached from the flask. For this purpose, cells were incubated with 1× trypsin solution at 37° C. for 5 minutes and then medium was added to stop the reaction. Cell suspensions were counted by means of trypan blue and centrifuged (4° C., 1400 rpm, 5 min). Cells were resuspended in medium and one part was subcultured, and another part was separated with the required amount of cells for chip cultures. After recentrifugation, the cell pellet was mixed with Matrigel® (3000 cells per µl Matrigel®) and the chips were filled with 45 µl cell/Matrigel® suspension per cell chamber. After 40 min of polymerization at 37° C., 3D cultivation medium was added (DMEM, 10% FBS, 1% antibiotic, 1% MEM NEAA, 1% ITS, 31.6 µg/ml L-ascorbic acid 2-phosphate, 2% HEPES). Chips were cultured at 37° C. and 5% CO2 for up to 4 weeks, and the medium was exchanged twice a week.
Results and Discussion In early passages, there are still substantially more immune cells present, which have an impact on micromass formation as the environment mimics an inflamed joint. FIG. 14A shows that the higher the passage, the smaller the micromass, which is due to better micromass formation. FIG. 14B shows that the micromass formed from passage 5 cells forms a much rounder and better formed micromass, while the micromass formed from passage 1 cells after 4 weeks rather consists of a cluster and does not form a characteristic denser outer layer towards the medium. The visual appearance of the micromass already gives substantial information about the state of the cells.

Example 3: Decrease in Size as an Indicator for the Redifferentiation of Chondrocytes Methods
Chip Production To clean the base of the chip, a microscope slide (76×26 mm) from VWR was first placed in a 2% Hellmanex® III solution and treated in the ultrasonic bath for 5 minutes. Subsequently, the solution was discarded and the procedure was repeated first with isopropanol and then with water. Finally, the microscope slides were dried with compressed air and in an oven for 1 hour at 80° C.

For chip production, 5 PDMS layers (76×26 mm) had to be cut out first. For this purpose, 0.5 mm thick PDMS film was inserted into the Roland DG CAMM-1 GS-24 cutter and the desired shape was cut out, which was removed with tweezers. Then, the individual layers were bonded together by plasma activation, starting with the microscope slide and the first layer of PDMS film. The strength of the bond was enhanced by heat treatment in an oven (80° C.).

Prior to using the chip, all chambers, channels and reservoirs were purged with 70% ethanol. The cell chambers were also coated with Lipidure®, an antifouling agent. Finally, the chip was sterilized with UV light.
Cell Culture Chondrocytes, purchased from Sigma Aldrich (C-12710), were cultured in culture flasks with chondrocyte growth medium from Sigma Aldrich (411-500) (37° C., 5% CO2). At 90% confluence, cells were detached from the flask. For this purpose, cells were incubated with 1× trypsin solution at 37° C. for 5 minutes and then medium was added to stop the reaction. The cell suspension was centrifuged (4° C., 1400 rpm, 5 min) and meanwhile, a sample of it was counted with trypan blue. The cell pellet was resuspended in medium and the required amount of cells for chip cultures was separated. After recentrifugation, the cell pellet was carefully mixed with fibrin (2000 cells per µl fibrin) and aliquoted with 30 µl each. For filling a cell chamber, 30 µl of thrombin (4 U/ml) was mixed with fibrin and immediately loaded into the chip. The chip was incubated at 37° C. for 15 min to form a solid 3D network. Subsequently, chip cultivation medium (DMEM, 1% antibiotic, 1% MEM NEAA, 1% ITS, 31.6 µg/ml L-ascorbic acid 2-phosphate, 2% HEPES) with different concentrations of FBS and TGF-β3 or chondrocyte differentiation medium from Sigma Aldrich (411D-250) was added. The chips were cultured at 37° C. and 5% CO for up to 4 weeks and the medium was exchanged every other day.

Results

Figure 15:
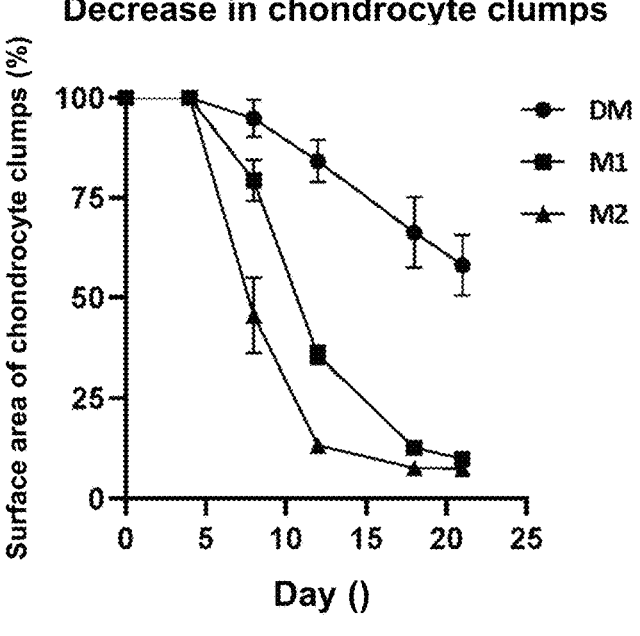
FIG. 15 shows the decrease in chondrocyte clumps over time with different media.

For a co-culture of chondrocytes and synovial fibroblasts, a medium was to be found that can be used for both cell cultures on the chip. The medium, starting from a synovial fibroblast culture on the chip, was modified to the effect that the serum concentration (1 and 10%) was varied and that TGF-33, which is necessary for the redifferentiation of chondrocytes, was added. These media were compared with a purchased differentiation medium. FIG. 15 shows that the size of the chondrocyte clump decreases much more over a time frame of 21 days with the self-defined media. In contrast, in the case of the purchased differentiation medium, the clump is still larger than 50% of the originally loaded construct after 21 days. It is apparent that with a lower serum concentration, the initial decrease is smaller, but after 21 days, the size is similar to those cultured with a higher serum concentration.

The invention claimed is:

1. A microfluidic device (1) for producing a three-dimensional cell culture, the microfluidic device comprising:
   a chamber (2) comprising a main chamber portion (5) and a secondary chamber portion (6) connected to the main chamber portion (5);
   a fluid channel (3) extending at least partially through the chamber (2) for providing and configured to enable a fluid to flow through the chamber (2); and
   a loading opening (4) configured to load hydrogel into the chamber (2), wherein the chamber (2) is connected to the loading opening (4) and is configured to be filled with hydrogel via the loading opening (4) up to a desired fill level,
   wherein the main chamber portion (5) and the secondary chamber portion (6) are configured so that, when the chamber (2) is filled with hydrogel up to the desired fill level, both the main chamber portion (5) and the secondary chamber portion (6) are filled with hydrogel,
   wherein the main chamber portion (5) has a main chamber portion bottom (8) and the secondary chamber portion (6) has a secondary chamber portion bottom (11),
   wherein the main chamber portion bottom (8) is formed at a lower height level than the secondary chamber portion bottom (11),
   wherein the secondary chamber portion (6) has a smaller volume than the main chamber portion (5).

2. The microfluidic device (1) according to claim 1, further comprising a connecting channel (7), wherein the main chamber portion (5) and the secondary chamber portion (6) are connected by the connecting channel (7), wherein the connecting channel (7) has a smaller cross section than the main chamber portion (5) and the secondary chamber portion (6).

3. The microfluidic device (1) according to claim 1, wherein the fluid channel (3) at least partially extends through the main chamber portion (5), wherein the fluid channel (3) comprises a fluid inlet (9) spaced apart from the main chamber portion bottom (8) in the main chamber portion (5) and a fluid outlet (10) spaced apart from the main chamber portion bottom.

4. The microfluidic device (1) according to claim 3, wherein the fluid channel (3) has a fluid channel bottom (16), wherein the fluid channel bottom (16) is formed at a higher height level than the main chamber portion bottom (8).

5. The microfluidic device (1) according to claim 4, wherein the fluid channel bottom (16) is formed at a lower height level than the secondary chamber bottom portion (11).

6. The microfluidic device (1) according to claim 1, wherein the loading opening (4) is connected to the secondary chamber portion (6).

7. The microfluidic device (1) according to claim 1, wherein the secondary chamber portion (6) is connected to the main chamber portion (5) on a side (12) of the main chamber portion (5) opposite the fluid channel (3).

8. The microfluidic device (1) according to claim 1, wherein the fluid channel (3) runs along a side wall (13) of the main chamber portion (5).

9. The microfluidic device (1) according to claim 1, further comprising a conduit (15) connecting the loading opening (4) to the chamber (2).

10. The microfluidic device (1) according to claim 1, wherein the chamber (2), the main chamber portion (5), the secondary chamber portion (6), the fluid channel (3), or a combination thereof comprises an antifouling surface coating.

11. A carrier (17) comprising the microfluidic device (1) according to claim 1.

12. A method of producing a three-dimensional cell culture or an organoid using the microfluidic device (1) according to claim 1, the method comprising loading the chamber (2) through the loading opening (4) with hydrogel up to the desired fill level.

13. The method according to claim 12, further comprising introducing cells into the chamber 2 through the loading opening 4 during the loading or after the loading or both during and after the loading.

14. A method determining an influence of a chemical compound or of a physical parameter or of both on cells of a three-dimensional cell culture using the microfluidic device according to claim 1, the method comprising:
   a) detecting a first state of the cells;
   b) contacting the cells with a chemical compound or changing a physical parameter within the microfluidic device or both;
   c) detecting a second state of the cells; and
   d) determining the influence of the chemical compound or of the physical parameter or of both on the cells by identifying a difference between the first state and the second state.

15. The microfluidic device (1) according to claim 1, wherein the fluid channel (3) is configured to enable a fluid to continuously pass through the chamber (2).

16. The microfluidic device (1) according to claim 10, wherein the antifouling surface coating is selected from the group consisting of a polyethylene glycol (PEG)-based polymer, a polysaccharide, agarose, a polyhydroxy polymer, poly(2-hydroxyethyl methacrylate) (poly-HEMA), 2-methacryloyloxyethyl phosphorylcholine (MPC), dextran, hydroxyethyl cellulose (HEC), a natural polymer, an S-layer protein, and combinations thereof.

17. The method according to claim 13, wherein the cells are selected from the group consisting of a stem cell, a primary cell, a fibroblast, a cartilage cell, an endothelial cell, an epithelial cell, an adipose cell, an induced pluripotent stem cells (IPS), an osteoclast, an osteoblast, and an osteo-
cyte or a combination thereof.

* * * * *